(12) United States Patent
Prokopp

(10) Patent No.: US 11,064,886 B2
(45) Date of Patent: Jul. 20, 2021

(54) DEVICE AND METHOD FOR THE MOBILE ANALYSIS OF EXCREMENT IN A TOILET

(71) Applicant: Thomas Prokopp, Bonn (DE)

(72) Inventor: Thomas Prokopp, Bonn (DE)

(73) Assignee: MEDIPEE GMBH, Moers (DE)

( * ) Notice: Subject to any disclaimer, the term of this patent is extended or adjusted under 35 U.S.C. 154(b) by 476 days.

(21) Appl. No.: 15/741,274

(22) PCT Filed: Aug. 3, 2016

(86) PCT No.: PCT/EP2016/068553
§ 371 (c)(1),
(2) Date: Dec. 31, 2017

(87) PCT Pub. No.: WO2017/021452
PCT Pub. Date: Feb. 9, 2017

(65) Prior Publication Data
US 2018/0184906 A1 Jul. 5, 2018

(30) Foreign Application Priority Data

Aug. 3, 2015 (DE) .................. 10 2015 112 678.8
Apr. 22, 2016 (DE) .................. 10 2016 107 486.1

(51) Int. Cl.
*A61B 5/00* (2006.01)
*A61B 10/00* (2006.01)
(Continued)

(52) U.S. Cl.
CPC ............ *A61B 5/0022* (2013.01); *A61B 5/117* (2013.01); *A61B 5/14507* (2013.01);
(Continued)

(58) Field of Classification Search
CPC ..... A61B 5/0022; A61B 90/361; A61B 90/70; A61B 5/117; A61B 5/14507; A61B 5/207;
(Continued)

(56) References Cited

U.S. PATENT DOCUMENTS

| 4,466,445 A | 8/1984 | Abrams |
| 5,184,359 A * | 2/1993 | Tsukamura ........ A61B 5/02241 4/314 |

(Continued)

FOREIGN PATENT DOCUMENTS

| DE | 3402488 C2 | 10/1984 |
| DE | 69117229 T2 | 9/1996 |

(Continued)

OTHER PUBLICATIONS

Machine translation of Fichtner Wolfgang, Intelligent toilet and method of operation, DE-102010061035-B4 (Year: 2012).*

(Continued)

*Primary Examiner* — David J. McCrosky
*Assistant Examiner* — Chanel J Jhin
(74) *Attorney, Agent, or Firm* — Bycer Law, PLC; Matthew L. Bycer

(57) ABSTRACT

A device for determining physiological data through analysis of human excrement in a toilet using at least one indicator and/or sensor, and a method for determining physiological data by analysis of human excrement in a toilet by measurement of urine and/or stool values, in order to achieve maximally universal use of the device, including in a wide variety of toilet designs, with reasonable design effort and manageable costs. A measurement system, in which an indicator or sensor can be brought into a measurement position, in which sufficient contact with the urine or stool to be examined occurs via an arm for each measurement, (Continued)

wherein the indicator or sensor is/are designed as (an) independent unit(s), and by a corresponding method in which a plurality of previously determined values are measured and then processed further and forwarded as applicable.

18 Claims, 8 Drawing Sheets

(51) Int. Cl.
| | |
|---|---|
| *A61B 5/145* | (2006.01) |
| *A61B 5/20* | (2006.01) |
| *G01N 33/487* | (2006.01) |
| *G01N 33/493* | (2006.01) |
| *A61B 90/00* | (2016.01) |
| *A61B 90/70* | (2016.01) |
| *A61B 5/117* | (2016.01) |
| *A61B 8/08* | (2006.01) |
| *B08B 7/00* | (2006.01) |
| *G01N 33/483* | (2006.01) |

(52) U.S. Cl.
CPC ............ *A61B 5/207* (2013.01); *A61B 5/4343* (2013.01); *A61B 5/4845* (2013.01); *A61B 5/4848* (2013.01); *A61B 5/4866* (2013.01); *A61B 5/6887* (2013.01); *A61B 8/5207* (2013.01); *A61B 8/5223* (2013.01); *A61B 10/007* (2013.01); *A61B 10/0012* (2013.01); *A61B 10/0038* (2013.01); *A61B 90/361* (2016.02); *A61B 90/70* (2016.02); *B08B 7/0057* (2013.01); *G01N 33/4833* (2013.01); *G01N 33/4875* (2013.01); *G01N 33/493* (2013.01); *A61B 5/4381* (2013.01); *A61B 2010/0003* (2013.01); *A61B 2010/0009* (2013.01); *A61B 2010/009* (2013.01); *A61B 2090/063* (2016.02); *A61B 2560/0223* (2013.01); *A61B 2560/0406* (2013.01); *A61B 2560/0462* (2013.01); *A61B 2562/0285* (2013.01); *A61B 2562/063* (2013.01); *A61B 2562/164* (2013.01)

(58) Field of Classification Search
CPC ... A61B 5/4343; A61B 5/4845; A61B 5/4848; A61B 5/4866; A61B 5/6887; A61B 8/5207; A61B 8/5223; A61B 10/0012; A61B 10/0038; A61B 10/007; B08B 7/0057; G01N 33/4833; G01N 33/4875; G01N 33/493
USPC .......................................................... 600/574
See application file for complete search history.

(56) References Cited

U.S. PATENT DOCUMENTS

| | | | |
|---|---|---|---|
| 5,625,911 A | 5/1997 | Nakayama et al. | |
| 6,602,574 B1 | 8/2003 | Daton-Lovett | |
| 9,810,686 B1 * | 11/2017 | Hall ..................... | G01N 33/521 |
| 2005/0261605 A1 | 11/2005 | Shemer et al. | |
| 2018/0184906 A1 | 7/2018 | Prokopp | |

FOREIGN PATENT DOCUMENTS

| | | | | |
|---|---|---|---|---|
| DE | 69520850 T2 | 3/2002 | | |
| DE | 60126448 | 6/2007 | | |
| DE | 102010061035 B4 * | 10/2012 | ........... | A61B 5/0402 |
| DE | 102010061035 B4 | 10/2012 | | |
| JP | H085631 A | 1/1996 | | |
| JP | 2001083147 A | 3/2001 | | |
| WO | WO2009035599 A1 | 3/2009 | | |
| WO | WO2009107988 A2 | 9/2009 | | |
| WO | WO2012077933 A2 | 6/2012 | | |
| WO | WO2012105748 A1 | 8/2012 | | |

OTHER PUBLICATIONS

Machine translation of DE60126448, Method and system for providing a home-based health service (NEC Corp.), Jun. 14, 2007.
Machine translation of DE3402488C2, Toilet Apparatus (Toto Ltd.),Oct. 4, 1984.
Machine translation of JPH085631A, Urine inspection stool and urine component data detector used for the stool (Nippon Pulse Gijutsu Kenkyusho), Jan. 12, 1996.
Machine translation of JP2001083147A, Device for Urinalysis (Matsushita Electric Ind Co Ltd), Mar. 30, 2001.
Machine translation of DE69520850T2 Method and device for measuring urine components (Arkray Inc.), Mar. 28, 2002.
Machine translation of DE102010061035 B4, Intelligent toilet and method of operation (Bits Zwickau Bueromat IT Systeme GmbH), Oct. 31, 2012.
Machine translation of DE69117229T2 Chair-like device for sampling and examining urine with swiveling conveyor (Toto Ltd.), Sep. 5, 1996.

* cited by examiner

DEVICE AND METHOD FOR THE MOBILE ANALYSIS OF EXCREMENT IN A TOILET

CLAIM OF PRIORITY

The present application includes subject matter disclosed in and claims priority to European PCT application No. PCT/EP2016/068553, filed Aug. 3, 2016, DEVICE AND METHOD FOR THE MOBILE ANALYSIS OF EXCREMENT IN A TOILET, and incorporated herein by reference, and also applications establishing priority, DE 10 2015 112 678.8 (filed Aug. 3, 2015), and DE 10 2016 107 486.1 (filed Apr. 22, 2016), a device and a method described with which mobile analysis of excrement is carried out in the toilet, incorporated herein by reference, which describe inventions made by the present inventor.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

STATEMENT REGARDING PRIOR DISCLOSURES BY THE INVENTOR OR A JOINT INVENTOR

Not Applicable

BACKGROUND OF THE INVENTION

1. Field of the Invention

The present invention relates to a device and a method for determining physiological data through analysis of human excrement in a toilet by means of at least one indicator and/or sensor by measurement of urine and/or stool values, as well as a use of such a device and of the above-mentioned method.

2. Description of Related Prior Art

Healthcare is becoming increasingly digitalised. Wearable minicomputers are now an integral part of the consumer world. They can gather a multitude of data and analyse vital parameters such as active and rest periods, blood sugar levels, weight, body fat values, etc., in real time. The devices are generally wirelessly connected to "mobile end devices" so that they can immediately evaluate the data concerning health, nutrition, and activity status. This represents a quantum leap for treatment and diagnostics. In future, the option of independent or distance observation of body data will more and more frequently replace costly follow-up consultations at the doctor's surgery or hospital.

The great market potential of the consumer product is, on the one hand, based on an ever-aging population and an increasingly health conscious population group, and their eagerness to gather their vital parameters. The data are mainly used preventatively for a comprehensive evaluation of the state of health and thus also for optimisation of individual lifestyles. On the other hand, the development is driven by trends such as early stage diagnostics, "eHealth" and telemedicine.

The majority of these analyses have in common the fact that they primarily measure and document values other than vital parameters. For this reason, vital parameters from inside the body or so-called "lab results" are often not taken into account due to the difficulty in acquiring samples and the costly analysis.

Thus, the analysis of blood or excrement (urine and stools) has a much broader significance concerning the actual state of health of the body than just the analysis of temperature, pulse or blood pressure. Indications of possible illnesses can also be found in the early stages, which in turn considerably increases the chance of a cure. A large number of people die unnecessarily from illnesses that could have been cured if there had been an early diagnosis.

As the analysis of blood according to the prior art is always invasive in the extraction process, i.e. extraction with a syringe or by scratching the outer skin, and also requires a certain standard of hygiene, this presents a substantial hurdle for unbiased daily or weekly use.

However, urine and stools are usually excreted by humans several times a day. Generally, defecation and urination are performed on a toilet.

By means of methods with reagents, it is possible to measure many values, such as pH values, protein, glucose, ketone bodies, bilirubin, occult blood, urobilinogen, nitrate and microbes, in a short amount of time. Thus, reagents, test papers and enzymes are required, which are often attached to supporting members (for example test strips).

The most common method for testing urine is a urine quick test. For this purpose, a test strip, on which there is a small square colour field, is immersed into the urine for a few seconds. Depending on the concentration in which the corresponding substance is found, the field of the test strip changes colour and can be measured. With urine tests it is possible to measure components, such as glucose, protein, hormones, vitamins or occult blood, in order to find indications of possible diabetes mellitus, nephrosis, hepatitis or other inflammatory diseases, a stone or tumour in the kidneys, bladder or urethra, or prostatitis. It is possible to detect the presence of various illnesses in the early stages in order to protect health through daily recording of concentrations of such substances in the urine. Pregnancy tests, ovulation tests and occasionally drug consumption tests are also carried out by means of urine tests. Urine tests are also suitable for checking metabolism in athletes or during a diet. However, blood alcohol levels can also be determined by measuring urine.

Alcohol absorbed by the body is disposed off in several different ways: up to 5% is exhaled in an unhanged form. Approximately 2% of the alcohol consumed is excreted through urine in an unchanged form, 1-2% of the alcohol is sweated out through the skin. Of the alcohol remaining in the body, approximately 90-95% is catalysed via alcohol dehydrogenase (ADH), first oxidised to acetaldehyde in the liver, then catalysed by the enzyme aldehyde dehydrogenase (ALDH) to acetic acid. The acetate is reduced to water and carbon dioxide via the citric acid cycle and respiratory chain with energy generation. The concentration-time relationship of blood alcohol has been thoroughly researched. As the toxicokinetics of ethanol are known, it is also possible to back calculate the consumption behaviour of the last few hours. On the other hand, ethanol disappears from the body relatively quickly. By far the greatest proportion of the alcohol consumed is reduced to acetic acid, but there are also numerous side reactions: in a non-oxidative side reaction (only approx. 0.5% of the total ethanol elimination) the alcohol is converted to ethyl glucuronide (EtG) with uridine 5'-diphosphobetaglucuronic acid ("active" glucuronic acid, UDP-glucuronic acid). Ethyl glucuronide is formed exclusively of ethanol as a direct alcohol metabolite. As no endogenous EtG levels exist, EtG is a very specific marker for alcohol consumption which can be detected in serum after just a single consumption of a small amount. The maximum EtG concentration is reached 3-10 hours after consumption, the maximum excretion rate after approx. 3-5 hours. The half-life period in the initial stage is 2-3 hours.

The reaction to ethyl glucuronide by the enzyme UDP-glucuronosyltransferase is catalysed, which reaction occurs in various forms in human metabolism. Essentially, two types are relevant for the breakdown of alcohol, which can be found in human organisms depending on genetic disposition: a fast-acting and a slow-metabolising type. An exact quantitative determination of the alcohol consumer from the detected EtG is therefore difficult without knowledge of the genetic variation of the test person. In addition, the time of consumption and the type of drink can still not be determined. Nevertheless, there is at least a partially quantitative relationship between the amount consumed and the resulting concentration of EtG: high EtG levels clearly allow the conclusion to be drawn that there was a correspondingly high consumption of alcohol. The excretion of ethyl glucuronide occurs in the kidneys, wherein small blood concentrations can be concentrated in the urine and can thus be detected. Research into the stability of urine tests proves that EtG content is reduced to less than 10% within 4 days. In comparison to blood alcohol, EtG can be measured for considerably longer. Certainly, the back calculation of previous blood alcohol content is very difficult, but the amount of amount of EtG measured definitely allows qualitative conclusions to be drawn on drinking behaviour.

Through access to additional datasets concerning a person (height, weight, genetic background, etc.) using corresponding algorithms a very precise approximation of the actual blood alcohol content can be generated from the urine. These data can be contributed by mobile end devices, for example. However, comparative projections of people with similar physiognomic or genetic features can also be used for this.

Diets or metabolism, for example in athletes, can also be checked through urine tests measuring ketone bodies. Ketone bodies are substances present in the breakdown of fat. In the narrower sense, acetoacetate, beta-hydroxybutyrate and acetone are to be understood. The liver in particular produces large amounts during the breakdown of fat. From the liver, the ketone bodies reach other tissue via the blood. They are quickly absorbed, so that normally almost no ketone bodies can be found in the blood. In principle, all three ketone bodies can be found in the urine through chemical analysis; in practice, only a urine strip test is usually carried out. In general, this is also sufficient. However, it must be ensured that conventional strip tests do not detect beta-hydroxybutyrate. However, there are certain disorders in which beta-hydroxybutyrate is particularly increased, and the other ketone bodies are less. For example, at the start of a ketogenic diet, the body can produce two different types of ketone bodies in somewhat similar quantities (acetoacetate and beta-hydroxybutyrate). At the beginning, both forms of these ketone bodies are needed by the muscles, etc. or are excreted through the urine. Over the course of this adjustment over a few weeks, the handling of the bodies changes with the two forms. The muscles stop directly absorbing beta-hydroxybutyrate and instead of this only absorb aetoacetate and reduce it to beta-hydroxybutyrate. Then they return it to the blood stream. Therefore, after a few weeks of the adjustment there can only be one form of ketone in the body. This fact must be taken into account when conducting the analysis.

In relation to drugs tests using urine, there are certain tests which only search for one substance, and other tests which test for a plurality of substances. In principle, test strips are provided for opiates/opioids (heroine, codeine, morphine, etc.), methadone, speed (amphetamine), ecstasy methamphetamine, cocaine, cannabinoids, barbiturates, benzodiazepines and tricyclic antidepressants.

In stool tests, human faeces are tested for possible pathogens and blood in the stools, among other things. The latter is always an indication of an illness or damage and a doctor should be consulted. However, there are also numerous physiological and vital bacteria in healthy bowels, in particular in the colon. Common detection methods include the guaiac test and immunological stool blood tests. A stool test can provide indications of various illnesses. These include in particular colon cancer, intestinal polyps or diverticulosis of the colon, diarrhoea, or disturbances to bile flow.

Overall, the statement confirms that a great deal can be revealed about the function and state of certain important organ systems of the human body by means of analysis of excrement.

For a better understanding of the invention, the existing, commonly used designs of toilets must also be discussed. Worldwide there are various types of toilet. Depending on the culture and area of application, the varieties can vary vastly. The most common examples are listed in the following.

So-called washdown flush toilets are toilets that are used while sitting, in which excretions fall into the water of a siphon which is located below the bottom of the user. Thus, the development of odour is low, as the water reduces the contact of the excrement with the room air. A disadvantage is that the water often splashes up to the bottom. This design is the most prevalent design in western countries. The flushing process of European and North American toilets differs in that while in Europe the water coming in when flushing transports the excrement away, in North America, in the siphons which often meander several times, a part of the flush water is introduced as a water jet.

A variation of this flush system is the cascade WC (also known as the cascade flushing toilet), where the drain to the siphon is right at the back (on the wall side). Water splashing is reduced by means of a ceramic tongue.

So-called shelf-style toilets are seated toilets, in which a sort of shelf is located beneath the bottom of the user, onto which the excretions fall. The flow to the siphon in a shelf-style toilet is forwards (to the centre of the space). The excretions first disappear into the sewage system when flushing over the siphon. The great disadvantage of this design is the strong odour development, which is why most public and private toilets since the 90s have been and will be converted to washdown flush toilets.

Currently, concerning this matter, a further change to rimless flush toilets is occurring. These operate without circumferential rims, under which dirt and bacteria can be found. This makes this toilet hygienic and easy to clean. The flush works with a special flush distributor which powerfully and as splash-free as possible guides the water to the right and left through the toilet bowl and transports it to the drain. On the market there are currently two different types of water rimless toilet bowls: type 1 is flush-rimless with a small apron on the upper edge of the bowl. In type 2, the flush rim is completely visible from above into the bowl, with no apron.

In Asia, so-called squat toilets are primarily known. With a squat toilet (also sometimes known as a standing toilet), the user does not sit on a bowl, but rather is in a squatting position. The toilet can therefore be a simple hole or a channel in the ground; nowadays there are also larger, pool-like constructions. Above all, squat toilets are widespread in Asia, southern Europe and Islamic countries. As no contact is made, these are often seen as being particularly hygienic. For those not used to them, use is quite difficult. Conversely, the use of a seated toilet can also pose a problem for those not used to it and who find the contact between the bottom and the toilet seat to be unhygienic. It should be noted that with a squat toilet—as opposed to with a seated toilet—the rectum is not bent.

Vacuum toilets are also known, which are used in aeroplanes, on ships, modern trains and in crewed space travel. Toilets in space are constructed based on a principle similar to a vacuum cleaner due to the lack of gravity. The opening is only around the size of the palm of the hand, and use must be practised.

With so-called "chemical toilets", the advantage is that the waste water must be disposed of less frequently. The disadvantage is the environmentally unfriendly chemicals, which are used to chemically treat the waste water. However, it is now also known how to treat the waste water biologically. Thus, microorganisms convert the waste water so that the water content can be used as service water again. These "biological toilets" allow long emptying cycles. The disadvantage is that the system can "overturn" if, for example, the toilet shell is cleaned with the wrong chemicals.

In the prior art, various forms of "intelligent" toilets are described. In almost all solutions the relevant technology is either integrated directly in the construction of the toilet and/or of the toilet seat. In addition, urine is collected, in order to be analysed separately. Between the years of 1987 and 2005, Toto LTD and its subsidiaries alone disclosed 25 patents for analysis methods in toilets which require a structural connection.

From DE 6012 64 48 T2 a urine test device with a biosensor is known which is replaceably attached inside a urine collection device. In addition, the urine device comprises a signal processor. The measurement data of patients is transmitted to a healthcare centre. Prevention and early indication are not mentioned. The described urine collection container is problematic from a hygienic point of view.

In DE 695 20 850 T2 a toilet is described which has a urine collection part and a measurement part for optically examining urine. The analysis of urine takes place in this system in a transparent, pipe-shaped flow cell.

DE 10 2010 06 10 35 B4 describes a toilet with an integrated measurement device for collecting physiological data of a user, wherein the toilet has a urine collection device provided in the inner volume of the toilet bowl together with a urine collection line. The analysis takes place in a cell (analysis unit) provided outside of the toilet bowl. A colour indicator supply and disposal system are also provided there which is connected to a colour indicator strip storage magazine or a colour indicator roll device. Principally, colours and clouding, as well as glucose content of the urine sample should be recorded.

In DE 34 02 488 C2 a toilet with a moveable biosensor, a microprocessor and a display for displaying the calculated results of the biosensor are described. The sensor receives excrement from a half height between the toilet seat and the toilet bowl. A moveable arm is provided for this.

DE 691 17 229 T2 discloses a toilet system which is also provided with a urine sample collection and analysis function. The toilet comprises a pivotable conveyor device for urine test strips. Strips are immersed in urine in a sample hollow space by the conveyor device, then raised up, optically analysed and subsequently disposed of in a waste bin.

With WO 2009 1079 88 A2 a toilet is known in which the urine can be analysed in real-time. By using specially adapted infrared ATR spectroscopy (Attenuated Total Reflectance) analysis can take place in the toilet adapted for this. Thus, an algorithm calculates the constituents of the previously collected urine using the collected data.

WO 2012 07 79 33 A2 describes a urine collection device for a urine analysis system mounted on a toilet seat. In this way, the urine is collected in a small pot which is guided into the toilet space by a rod driven by an electric motor. The urine is taken back to the device in the toilet seat for analysis.

WO 2012 10 57 48 A1 also discloses a solution through a toilet seat. Thus, urine test strips are transported between the legs of the person sitting on the toilet seat by means of a sophisticated mechanism consisting of an input slit, an input module and a carrier system. Subsequently, after analysis, the test strip is guided outside again by means of a discharge module. A cleaning system takes care of the hygiene of the machinery.

There are very few devices which take into account mobility during use. WO 2009/35599 A1 describes a device that can be attached to several types of toilet which collects urine and then carries out an evaluation. For this purpose, there is a urine recipient and a urine collection vessel which, however, entail various problems with hygiene. The designs are largely and flatly attached to the toilet in parts. No indicator is used with this device. It is not required for the simple, discreet use by a user.

US 2005/021605 A1 describes a device which can be attached to different toilet types. It first collects the urine in a type of vessel and then evaluates it. Nothing is mentioned about exact calibration or sampling with different physiognomies. There remains doubt as to whether it is actually possible, during a normal toilet use to reach the vessel attached on the side without causing unhygienic splashing. The previously described limitations and problems therefore also remain in this design. The analysis is not carried out by indicators, by optical evaluation in the chamber supported by various lighting methods.

For successful use of a regular, automated inspection of excrement, "normal" toilet use should not be substantially disrupted. In addition, a certain hygiene standard should be expected. If the toilet user must come into contact with the excretions themselves, bag them or remove them in another way, this poses an extremely high barrier. Almost no one, who is not obliged to do so, would regularly choose of their own free will to put themselves through such an undertaking. Admittedly, the challenges of complex installation and use of previous implementations, as well as the structural changes necessary with the majority of the solutions, are one of the most significant barriers to widespread use. In particular, many users do not want the effort of removing their old toilet and replacing it with a new, "intelligent" toilet.

In addition, no known implementation offers any solution for bridging the gap to current or future processing and communication methods, for example through mobile end devices. The visualisation, preparation and intelligent further processing is not obviously provided in the form of apps or modern software applications.

On this basis, the object of the invention is to develop and further develop the initially mentioned device and method for determining health data by means of analysis of human excrement in a toilet by measuring urine and/or stool values in such a way that, with acceptable constructive effort and manageable costs, a universal as possible use and thus a wide application, also with different toilet designs, can be achieved. In addition, mobile use of the device is desirable.

SUMMARY OF THE INVENTION

The solution according to the invention provides a plurality of variations for analysis. However, they all have in common that they allow subsequent use by means of simple retrofitting of existing toilets. The plug-and-play nature plays a very important role in the widespread establishment of the idea according to the invention and for the acceptance of a regular use.

The invention comprises a plurality of different measurement systems: from simple, manually operated measurement devices to electrically driven devices which carry out the measurement automatically. In addition, evaluation can take place with all systems. In the simplest form as a simple reference scale, but in most cases with the aid of a computer. Frequently, the systems communicate their data to evaluation devices. These are either directly connected to the system and exclusively designed for this purpose or they provide (most also primarily) other functions and the system only uses the calculation and visualisation capacity of these (already available to the user) mobile end devices.

With regard to the use of the device, it is very important to know the exact time of the measurement. Particularly with older people, sitting on the toilet seat does not necessarily mean that urine comes straight away. For various reasons, this can take different lengths of time depending on the various users. In a preferred embodiment of the device a plurality of the above-mentioned optoelectrical or sonographic methods can therefore be used and partially combined with each other in order to determine the optimal measurement time.

A further variant for determining the measurement time is the use of a heat sensor on the device. At corresponding temperature differences or when reaching an exact target value (for example the temperature of urine) the measurement is carried out. A further method is via the determination of sounds (for example splashes) which are characteristic of excretions. It is also possible to determine the measurement time through optical measuring technology (for example reflection). A light barrier and/or a laser are direction at points in the toilet where excrement will arrive. Through the change of the optical properties of the surface of the measurement point through excrement, the measurement is carried out.

A further teaching of the invention states that with optoelectrical evaluation and analysis methods the process of the indicator reaction can be followed over time. Capturing a plurality of images per second from the time of the first sample contact until the end of the reaction with the indicator/sensor under certain circumstances allows conclusions to be drawn regarding the quantity, but also the quality of the constituents in the excrement. Many indicators can react to different concentrations over a period of time.

To ensure clear user identification and data security, in a further embodiment a fingerprint sensor or voice recognition can also be provided on the device.

BRIEF DESCRIPTION OF THE DRAWINGS

In the following, the invention is explained in detail using preferred exemplary embodiments. The figures show the following.

DETAILED DESCRIPTION OF THE PREFERRED EMBODIMENTS

Figure 1A:
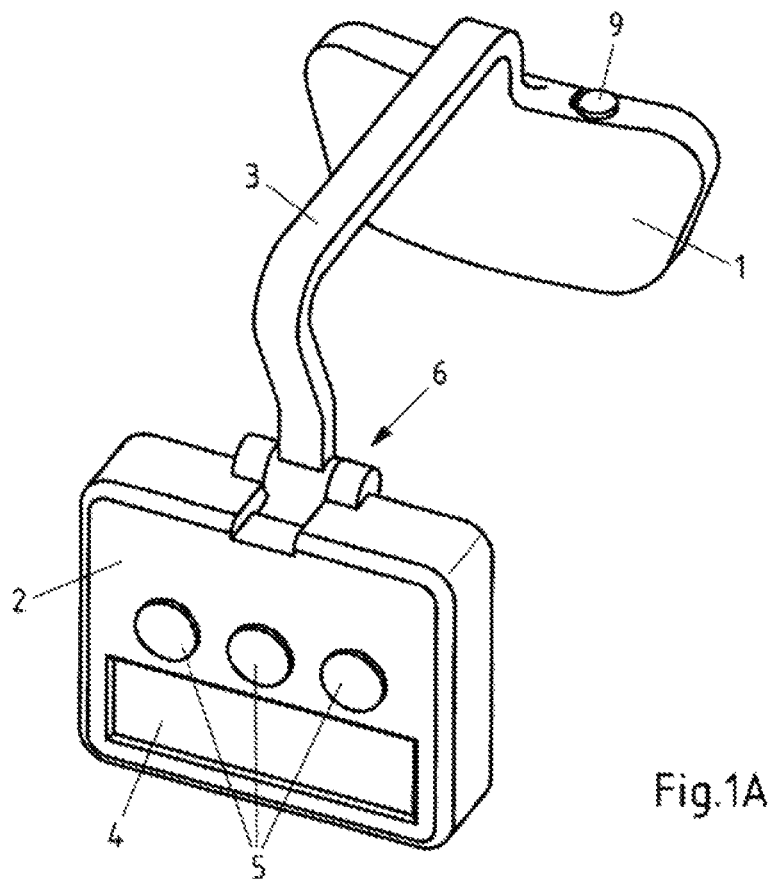
FIGS. 1A and 1B show a first embodiment of the device according to the invention, in perspective view.

For better understanding, in the following, essential aspects and components of the embodiments and design variants are described in detail:

1. Analysis Device

"Analysis device" refers to the entirety of the system components arranged in and on the toilet. In particular, these are combined in a physical location (the device housing). However, it can also be that case that, for example, the optoelectrical unit and the sensor arm are located in two different device casings. The relative distance between each other can therefore also vary. The communication or coordination of the system parts with one another is carried out via radio communication.

Installation of the analysis device on or in the toilet can be achieved by an adhesive, glue, or by means of a hook or bow device similarly to how a urinal block or toilet cleaning device is used.

In addition, it is also conceivable to attach the measurement device to a suitable position in or outside of the toilet with suction pads, magnetism (directly on stainless steel toilets or with counter-magnets on normal toilets), adhesive devices or other commonly used attachment methods. The location of optimal attachment varies depending on the design of the toilet; in a standard washdown flush toilet it is preferably arranged directly on or below the flush rim in order to save space if necessary and to reduce the distance to the measurement area in the toilet. In modern, rimless toilets, the device is positioned as far above the flush join or the stream of water so that there is no continuous contact with the flush water. The attachment methods are identical in principle. It is also conceivable to form the housing flexibly with regard to material so that it optimally adapts to the toilet shape. In a simple case, this effect could also be represented by a modular construction of the housing, in which individual areas are connected to each other by hinges or moveable elements.

2. Indicator/Sensor

Different devices and methods can serve as an indicator/sensor.

The most common method functions using test strips, test paper or in the broadest sense using single-use test carriers. Thus, a test carrier is prepared so that it can perform analyses. By changing the indicator, the possibility of analysis of urine is presented. The indicator is either evaluated at the location and where contact is made (usually by an optoelectrical or sonographic unit) or guided back onto or into the device for further analysis. Generally, the test carrier is used up after a single use and is then disposed of.

In addition, there are multiple-use indicators, for example nanobiosensors, which do not wear out after a single use and thus can be used multiple times. Measurement is generally carried out via electrical signals.

The presentation locations of the indicator can be from the location of leaving the body to the drain. In particular, in commonly used versions it is either in the siphon, just above it or in particular in the lower front area.

3. Calibration and Adjustment Calibration refers to the establishment and documentation of deviations in the display of a measurement device or a control unit from the correct value of the measurement. By adjustment the measurement is adjusted or harmonised so that the measurement deviation from the actual value is as small as possible and lies within the device specifications. In the present case, a plurality of situations are known in which one of the two measures is necessary. Often, adjustment and calibration are very closely associated with each other.

The first case presents itself in the installation of the device on the toilet. Depending on the design of the toilet, it provides a large or small installation window on the left or right rim of the toilet. The sensor arm can only reliably and precisely reach the optimal location for taking samples within this window. This location can be determined with knowledge of the toilet model, the basic design or with the aid of the optical measurement instruments on the device. The feedback to the user that the optimal installation location has been reached can for example be carried out visually or audibly.

Due to different design of toilets, the optimal location for taking the sample must also be determined in each case. This also occurs through knowledge of the toilet model, the basic design or with the aid of optical measurement instruments. In addition, the extended length of the sensor arm is determined, as well as the angle at which the indicator is optimally presented on the toilet wall. Here, the supported sensor arm can extend and as well as the optical identification, a pressure sensor identification is also made possible as soon as the arm touches the toilet wall, for example. Measured settings are stored in order to make reinstallation easier, for example when taking out the device to clean the toilet. Recalibration following bad sample taking/results is also possible after a certain use time or number of uses.

4. Triggering the Measurement
Triggering of the measurement can be carried out by the following mechanisms, which can also be combined:
  Triggering by movement of a lever or switch which is either directly connected to the system or alternatively connected by cable/radio communication.
  Light barrier/optical unit which analyses if urine/faeces/indicator enters the analysis area.
  Triggering by a mobile end device.
  Pressure sensor for weight on the toilet component (for example body weight on the toilet seat) or foot-floor contact at a urinal.
  Acoustic signal: for example, a call, a tune or a whistle.

5. Sensor Arm
The indicator/sensor is presented at the most suitable position within the toilet bowl by the sensor arm. Depending on the design, in the majority of cases this is at one of the deepest points, just above the siphon water.

The presentation can be carried out according to various principles. In the broadest sense, it is a device which bridges the distance between excrement and the indicator/analysis device. In addition, the device is provided with a holder or a capture unit for the indicator/sensor.

6. Measurement Units
The measurement unit can function in different ways depending on the medium to be measured and/or the indicator used.

6.1 Optoelectrical Reading of an Indicator/Sensor
Using this method, the indicator/sensor is read by an optoelectrical or even an optical (reading) unit. This term refers in the broadest sense to all products and methods which as well as the recording of images also allow the conversion of electronically received data and energy into light emissions and vice versa. Such devices and methods are, for example, traditional photographs (preferably digital), imaging methods from medicine, confocal technology, laser scanning, thermography, terahertz radiation, etc.

It is very possible that for privacy reasons, users would not wish to see or have saved large-sized photographs of the inside of their toilet. Therefore, the optoelectrical recording can possibly be carried out in a very focused way on the indicator or in a suitable format (for example schematized).

Evaluation directly on the sensor arm provides a reasonable alternative. In this way a small camera is fixed directly on the front part of the sensor arm or the guide sleeve for the sensor arm and can thus carry out evaluation directly when the indicator unit makes contact with the excrement. The installation of light sources, e.g. LED, can thus also be supported on the end of the sensor arm. Thus, optimal lighting of the indicator unit is ensured. The camera can take individual pictures or a series of pictures so as to also document the process.

6.2 Sonographic Reading of an Indicator/Sensor
The term reading via a sonographic unit, in the broadest sense, combines all products and methods which make it possible to determine values using soundwave technology. Sonography is therefore mainly based on the echo principle. A directed (ultra)sound is transmitted and more or less strongly reflected from the consecutive layers of the connected object (for example air-coupled ultrasound testing technology). The layer structure of the object can be reconstructed from the elapsed time of the reflected signal. There are particular advantages over optoelectronic technology if, for example, optical methods cannot be used due to bad lighting of the surface.

6.3 Electrical Measurement of an Indicator/Sensor
Above all, with nanobiosensors, measurement takes place using electrical currents, i.e. also their strength and length. For example, when a receptor makes contact with an effector, an electrical impulse is created which is then measured and evaluated.

6.4 Optical Volume and Weight Measurement of Excrement
With the support of one or more optical (for example 3D scanners) or sonographic units, the system can measure the height, width and length of a body with a very low tolerance rate. The accuracy of the measurement can be increased up to 99 percent by a further camera. As well as the volume measurement, the weight can also be determined. All of the data can, for example, be managed on a mobile end device and if necessary also shared with others. Preferably, we can carry this out in shelf-style toilets, but it can also be implemented in other toilet types.

6.5 Process Measurement

The optoelectrical evaluation and analysis methods with which the urine sample is tested provide the option to follow the process of indicator reactions over time. This is carried out, for example, by recording several images per second. This additional, temporal information under certain circumstances allows conclusions to be drawn regarding the quantity, but also the quality of the constituents in the excrement. Many indicators can react to different concentrations over a period of time.

7. Magazine/Indicator Compartment

In most embodiments an indicator is used which is used and then must again and again be "reloaded". In this way, depending on the wishes of the customer, different tests can be carried out. Thus, a device can have a plurality of magazine compartments into which the different tests can be "loaded", for example a magazine with tests for standard urine values, one with pregnancy tests and one with ovulation tests. When using the toilet, the customer selects, usually by pressing a button on the control unit, which test should now be performed. For the measurement of urine, urine test strips can be used as they can be obtained everywhere in pharmacies. These strips can, as long as the particular device variation allows it, be loaded into the system in defined quantities. For each test, the device takes a strip from the magazine (this occurs through simple gravity, i.e. drops into the emission by means of negative pressure of a spring, a slider, etc.), and presents it to the user in the described way. A revolving system could also be conceivable here, in which the strips are sorted into chambers. However, due to the lack of space alone, smaller test slides are usually provided in a magazine especially adapted for the use.

Thus, a disposal compartment ("collection unit") can also be arranged on the inside of the toilet, in which compartment the used indicator units can be disposed of. If this relates to biodegradable material, for example, disposal by flushing is also possible. A liquid indicator or indicator in roll form that can be ripped or separated can also be used.

8. Evaluation Device

The "evaluation device" is like the "brain" of the system. The evaluation device takes the data generated by the analysis and compares it, for example, to reference data from a database. In a common variant, this is a type of minicomputer with performance features similar to those of a smartphone. In an extremely slimline embodiment of the analysis device in or on the toilet, computing power can also be provided from "outside" and only the "raw data" of the analysis is provided to the end device. An application which runs on the end device prepares all the relevant data and visualises these. Devices for visualising are in particular mobile end devices.

Mobile end devices or mobile computing refer in the broadest sense to products or methods which allow electronic data processing on wearable computers. These include, for example, smartphones, laptops, tablets, or wearable devices such as glasses, fitness bands, watches, smart clothing and minicomputers in the human body; items that are indispensable in our daily lives and in the future.

9. Communication Device

The communication device is preferably a component of the analysis device. The transmission of data to end devices for visualisation is carried out from there either via cable-connected or wireless transmission standards, as are usually used in a domestic environment. For example, Bluetooth, WLAN, low-energy transmission standards, etc. Acoustic or light signals could also be conceivable if they can be incorporated into and handled by the communication device.

10. Visualisation

Apart from visualisation via software applications on mobile end devices, a simple monitor would also be possible which directly visualises the values and data, and if necessary forwards them to a suitable data storage device. The monitor can either be directly attached to the analysis device or separate from it on another, more visible location, for example at eye level on a wall next to the toilet. The information is transmitted by the previously described communication standards.

In particular for older people, it is suggested that the values are printed on a kind of voucher from the device (for example on thermopaper). Critical or notable values can thus be immediately highlighted. With this early indication, users can then seek medical advice for more precise interpretation of the conspicuous values.

11. Energy Supply/Energy Storage

The energy required to operate the system is not obtained from direct connection to a conventional power outlet. Working inside or in close proximity to toilet flush system with energy that could potentially kill a person does not seem advisable. By implication, this means that the system must draw its energy from elsewhere. First and foremost, operation with batteries or accumulators is referred to. Here, all commonly used formats of batteries can be accommodated in terms of size in the device. For example, AA, AAA, button cell, etc. The batteries can either be rechargeable or disposable. Solar power (usually coupled with batteries) in particular can also be considered as a further form of energy supply. Similar to as known from pocket calculators. A cell unit supplies the whole system with the necessary energy, either attached directly to the system or externally (then connected with a cable).

12. Hygiene

In the present case hygiene refers to the measures for cleaning, for disinfection and for prevention of contamination, in particular of the device, but also the toilet.

To achieve this, there are several approaches which for the most part can be combined with each other:

Generally minimal construction of the device on the inside of the toilet. This provides fewer contact surfaces for contamination.

Very short resting time of the sensor arm when collecting the sample. Combined with a very thin sensor arm the possibility of picking up urine and germs is significantly reduced.

Vibration of the sensor arm to dispose of the test sheets and also to clean the sensor arm.

The housing contains a protective cover which can be regularly replaced. The "old" cover is disposed of with normal waste.

Modular construction. Thus, individual parts can be cleaned separately or replaced if necessary.

Advantageous material coating. This generally makes it difficult to pick up unwanted substances.

UV light sources on the device. So-called "far" UV light is able to eliminate 99.9 percent of all bacteria and pathogens on a surface.

In a preferred embodiment the sensor arm is formed of a preferably rollable element which can be moved in the measurement position. In a further embodiment of the invention the sensor arm has a self-stiffening property.

In this way the sensor arm rolls out and forms an "arm". After a measurement has occurred the element rolls up and the "arm" is stowed away again. The material used for this has an inherent tension which, by means of mechanical deformation such as guideways, guide pulleys or guide lips, either leads to stiffening of the "arm" or makes the "arm" flexible and rollable again. The stiffened arm can be formed as a closed tube or be half open. At the end of these elements there are—as in the other preferred embodiments—retainers for taking up, transporting and disposing of the indicator. This version is space-saving and less fragile than other mechanical implementations. The length of the arm can be very variably formed as the space required for the rolled-out elements in the mobile device practically depends on the "arm length".

A self-stiffening "arm" that can be rolled out is already known for this and is, for example, described in U.S. Pat. No. 6,602,574 B1.

The self-stiffening sensor arm is reversibly configurable between a wound-up and an unwound form. The element stiffens when rolling out and presents the "sensor arm". The stiffening can be achieved by a corresponding selection of material which for example comprises tensile and/or pressure forces about the extendable axis. In addition, the material can, for example, form a circular shape about the extendable axis. However, the same effect can also be generated by a guide lip. Thus, the element which is rolled up in a similar way to an extendable tape measure, when leaving the housing is forced by the device into rolling out so that it is brought into a shape with a round or square cross-section and thus directly brings about a stiffening. This means that the geometry of the element generates the necessary stability for the analysis. As in the other embodiments, at the end of the element there are retainers for taking up, transporting and disposing of the actual indicator.

In a further preferred embodiment, the propelled end of the sensor arm is attached to the outside of the toilet and rolls out almost over the retainer (between the toilet bowl and the seat) into the inside of the toilet. Preferably a guide provided for this is attached inside the retainer. This could, for example, be an encasement such as a sleeve or a plastic holder, but simple clamps or guide items are possible. A form of Bowden cable can also be used for this variant. This moves per se in a sheathing and can be long and flexibly formed.

Technologically, the optical measurement technology can also be carried out in a further preferred embodiment through (cell) cameras in combination with (optical) reference samples (such as lines, grids, etc.). High-quality three-dimensional images of areas inside the toilet can be made by a corresponding spatial resolution and mapping, and higher speed. Apart from the taking of measurements, this can above all be used for measuring the volume and mass of excrement. For urine this may mean even at the time of leaving the body to the point of contact with the toilet. Using algorithms, the volume, the mass and the volume and mass flow can be calculated with the collected data.

In a further preferred embodiment, the calibration and adjustment of the device and the sensor arm can be completed with the aid of different information sources. Apart from data from previously described sensors that determine the locations and relative distances to the target positions, information from knowledge of the toilet model or comparison of the basic design are also used. The feedback to the user can occur visually or acoustically.

In a similar way, in a further preferred embodiment, the optimal position for taking the sample is determined. In addition, the extension length of the sensor arm, as well as the angle at which the indicator is optimally presented on the toilet wall are thus determined. Apart from use of the previously described information sources, for this purpose the sensor arm can extend and allow detection via a pressure sensor. This occurs if the arm comes into contact with the toilet wall, for example. Measured settings are saved with all calibrations and adjustments in order to make reinstallation easier, for example when taking out the device to clean the toilet. Recalibration following bad sample taking/results is also possible after a certain use time or number of uses.

The device for stool analysis is similar to that for urine analysis. Both tests can be covered by one device (combi-device). However, it is also possible to provide just one, specific device for this. The advantage is that the sensor arm is not required for this.

Specially prepared toilet paper and hygienic paper are used for stool analysis. The paper has the property to change its surface structure and in particular colour after contact with stools and the constituents contained in them, above all those which should not be present in healthy stools. In this connection the optoelectrical or sonographic unit can detect this change.

Therefore, it can be necessary (particularly with combi-devices) to recalibrate the measurement unit for this reason. For example, the focus of a camera can change more towards the siphon in a washdown flush toilet.

In a further preferred embodiment, an analysis is used, for example, in which the indicator/sensors, in contrast to the previously described solutions, are not used up. For this purpose, the "sensor arm" is provided with a multiple-use sensor in the place of a single-use indicator. For the underlying invention referred to, it will behave so that either a universal "sensor head" can carry out all conceivable analysis, or that the heads can be changed depending on the measurement desired. Preferably here, there is a type of magazine variant, in which a different "measurement head" is attached to the end of the sensor arm depending on the measurement purpose. Here "measurement head" can refer to technical implementations which all have in common that they allow the measurement of one or more different substances. Implementation applications can, for example, be two antennae as in liquid capacity level sensors, or just a small sheet with different nano-receptors, or even a type of "little hat" for pressing onto the end of the sensor arm. The information is gathered by the sensor and electronically forwarded. Either to a minicomputer in the analysis device or even directly to a mobile end device.

A specially treated area (for example with nanobiosensors) is used as a particular form of the multiple-use indication, which is installed in the toilet, preferably where urine will flow over it. After contact with urine, the area changes by means or colour and/or structural change in such a way that the measurement method described in the following can be read. An advantage of this variant is that the sensor arm is not required at all.

In a preferred embodiment the indicator unit is used in a liquid form. Thus, the indicator enzyme is transported from the main unit to the end of the sensor arm by means of a tube system. There the enzyme is distributed to a grid. Through the specially dimensioned grid and material, the enzyme is distributed and adheres over the whole area. This grid is brought into contact with excrement by means of the sensor arm and lets the enzyme react correspondingly. The reaction is immediately evaluated by the already described optoelectrical unit. In this connection, the grid is cleaned through contact with flush water.

In a further preferred embodiment, the indicator is in the form of rolls, from which one required piece is separated during analysis. The rolls are located in the already mention magazine in a housing depending on the embodiment either on the inside or the outside of the toilet. The separation of the indicator parts required for the measurement can occur through commonly used cutting mechanisms or through previous preparation of the roll (for example perforations for ripping). Thus, some space can be saved inside the device and more rolls can be provided therein. It could also be possible to use indicator rolls with a plurality of indications on one roll.

In a preferred embodiment, an individual indicator strip is manually fed in the device for each measurement process. This occurs via a hopper opening, an intake (gap) or an influx gate which are positioned in an easily accessible position on the device. After the feed of the indicator, this is transported from the device to the measurement position inside the toilet and positioned for this purpose. The transport between the outside of the toilet and the sensor arm on the inside is carried out either by gravity, by negative pressure, by (motorised) rollers, spring tension or by a firm press from the user. The transfer to the already described sensor arm is carried out on the inside.

In a further preferred embodiment, the indicator units are again disposed of by an incorporated magazine. Thus, the indicator units are guided back into the disposal magazine after making contact with excrement by means of the sensor arm and subsequent evaluation. This can either be a magazine provided exclusively for this purpose or a part of the indicator device magazine which provides space for the used indicator unit when extracting an indicator unit. Used and unused indicator units are thus separated from each other. The disposal magazine can be easily replaced.

Colour and pattern differences can function as indication in all indicators mentioned. For example, an indicator can contract, the surface can become rougher, a shape can be formed thereon (for example it is pulled together to form a ball), etc. In terms of reading, here, apart from optoelectrical methods, it is also possible to determine the values by means of soundwave technology (for example sonography).

In an alternative embodiment, the indicator or sensor can be brought into the measurement position by a sensor arm guided by a guide sleeve. In this way, it is possible that the sensor arm can be essentially thinner, which significantly reduces the construction size and risk of contamination.

The removal or reduction of contamination can also be achieved by shaking or vibration of the sensor arm. Through fast, jerky movement of the sensor arm, especially caused by the motor, contamination can be reduced. The shaking movement can occur in various axes.

A further variant to reduce contamination of the sensor arm is a wiper device for urine when retrieving the sensor arm. Thus, the sensor arm is mechanically, chemically or electronically cleaned. In a further preferred embodiment, the sensor arm is freed of excrement when retrieved through "brushes". The brushes are formed in such a way that they can clean themselves or can be regularly replaced or serviced. In principle, the surface of the sensor arm is arranged in such a way that as little excrement as possible adheres to it. This occurs through geometry and/or a coating. These measures can already achieve the desired effect (e.g. the lotus effect) on specially functionalised surfaces.

To reduce the contamination from excrement on the device, in a further preferred embodiment a protective sleeve is provided which can be replaced when there is a corresponding amount of contamination present or on a regular basis. The protective sleeve is in particular stretched over the sensor arm. Thus, when a lot of contamination of the sensor arm occurs, the protective sleeve can simply be disposed of and a new one attached.

In a further preferred embodiment, the calibration and adjustment of the device and the sensor arm can be completed with the aid of different information sources. Apart from data from previously described sensors (optoelectrical or sonographic) that determine the locations and relative distances to the target positions, information from knowledge of the toilet model or comparison of the basic design are also used. The feedback to the user can occur visually or acoustically.

In a similar way, in a further preferred embodiment, the optimal position for taking the sample is determined. In addition, the extension length of the sensor arm, as well as the angle at which the indicator is optimally presented on the toilet wall are thus determined. Apart from use of the previously described information sources, for this purpose the sensor arm can extend and allow detection via a pressure sensor. This occurs if the arm comes into contact with the toilet wall, for example. Measured settings are saved with all calibrations and adjustments in order to make reinstallation easier, for example when taking out the device to clean the toilet. Recalibration following bad sample taking/results is also possible after a certain use time or number of uses.

A further teaching of the invention states that a UV light source is provided for the disinfected cleaning of the device and/or the entire toilet. This light source can be part of the device or simply connected to it and be arranged on another position, for example on the inner side of the toilet bowl, opposite the device.

Figure 1B:
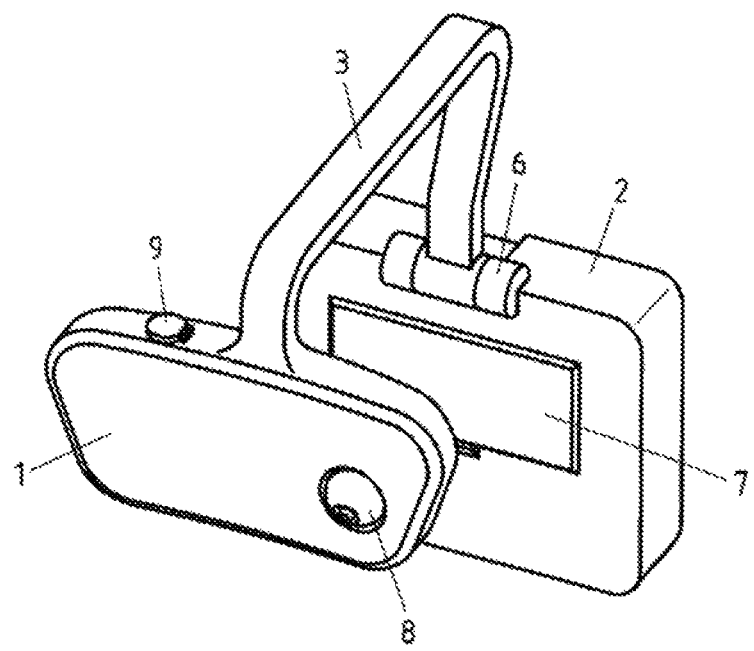

FIGS. 1A and 1B show an example of a first embodiment of a device according to the invention in different perspective views. Thus, the device also comprises, apart from a housing 1 for incorporating indicators (not shown here), a control unit 2. In the represented and thus far preferred embodiment, the housing 1 and the control unit 2 are connected by means of a retainer 3. The retainer 3 is a particularly suitable construction because, as well as connecting the housing 1 and the control unit 2, it can also be used for attaching to the edge of the toilet bowl. However, them are also many other plausible attachment solutions for installing the device according to the invention, such as suction pads, glue, or other similar adhesive connecting elements of the invention.

The control unit 2 visible from the operating side in FIG. 1A comprises a control display 4, three operating elements 5 for releasing and if necessary adjusting the device, as well as a hinge 6 for pivotable movement of the retainer 3 relative to the control unit 2. Thus, the control display 4 can be adjusted by the user for improved operation.

A cover 7 of a compartment for holding batteries or accumulators is visible on the visible rear side of the control unit 2 in FIG. 1B. The housing 1 is further provided with a measurement unit 8, which can be, for example, achieved as a camera (optoelectrically) or/and sonographically. A magazine for holding a plurality of indicator strips inside the housing 1 is closed with a cover 9. The housing 1 can also be provided with a light source (not shown).

Figure 2:
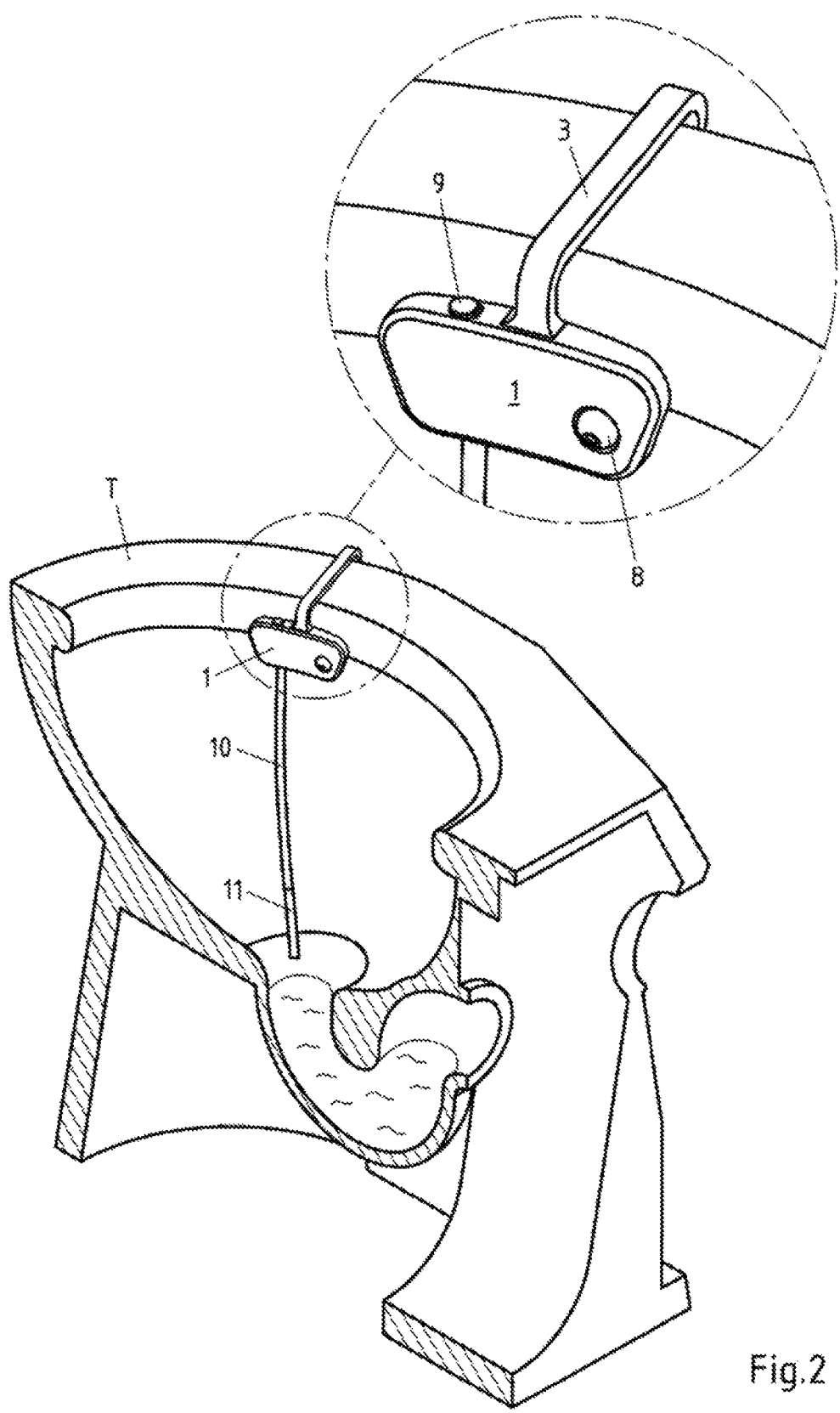
FIGS. 2 and 3 show different views of the embodiment of the device according to the invention shown in FIGS. 1A and 1B, in the perspective of inside a toilet bowl.

In FIG. 2 a possible arrangement of the device described in detail in FIGS. 1A and 1B is shown in a (represented in cross-section for a better view) standard washdown flush toilet T, and in a perspective view diagonally from behind. The retainer 3 as well as the housing 1 with measurement unit 8 and cover 9 of the magazine compartment are visible. A sensor arm 10 and an indicator 11 are also visible below the housing 1. The actual indicator 11 is arranged at the end of the sensor arm 10, which after contact with excrement and evaluation by the measuring unit 8 can be disposed of via the flush system of the toilet T. In the represented exemplary embodiment, the sensor arm 10 can be telescopically extended out of the housing 1.

Figure 3:
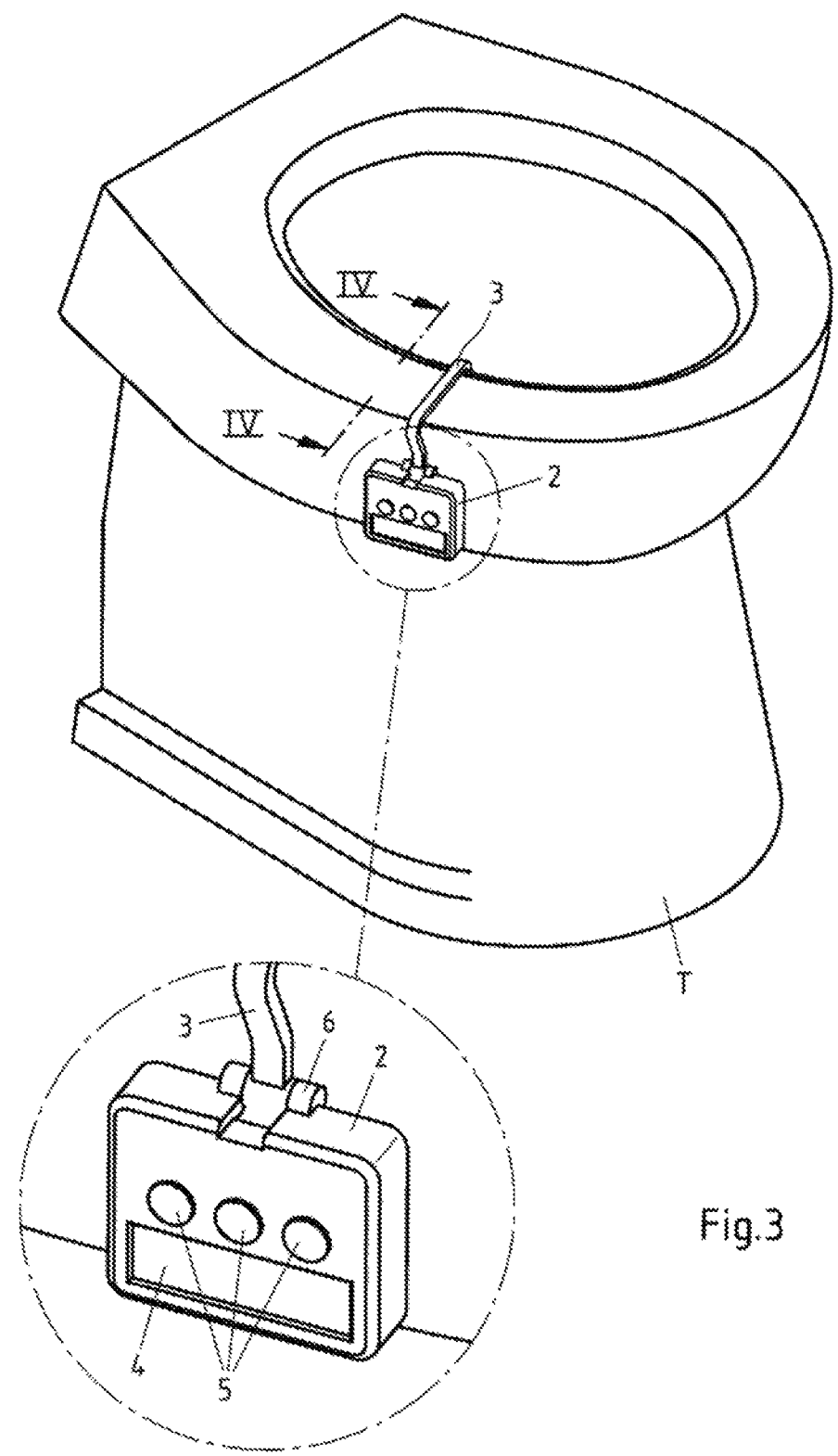

FIG. 3 shows the device from FIGS. 1A and 2A in a perspective outer view diagonally from in front. Apart from the retainer 3, above all here the control unit 2 with the control display 4 and the three operating elements 5 for installing and if necessary adjusting the measuring process are visible. It is clearly visible that the device according to the invention is barely noticeable from the outside and can be easily attached to the edge of toilet bowls (any shape).

Figure 4:
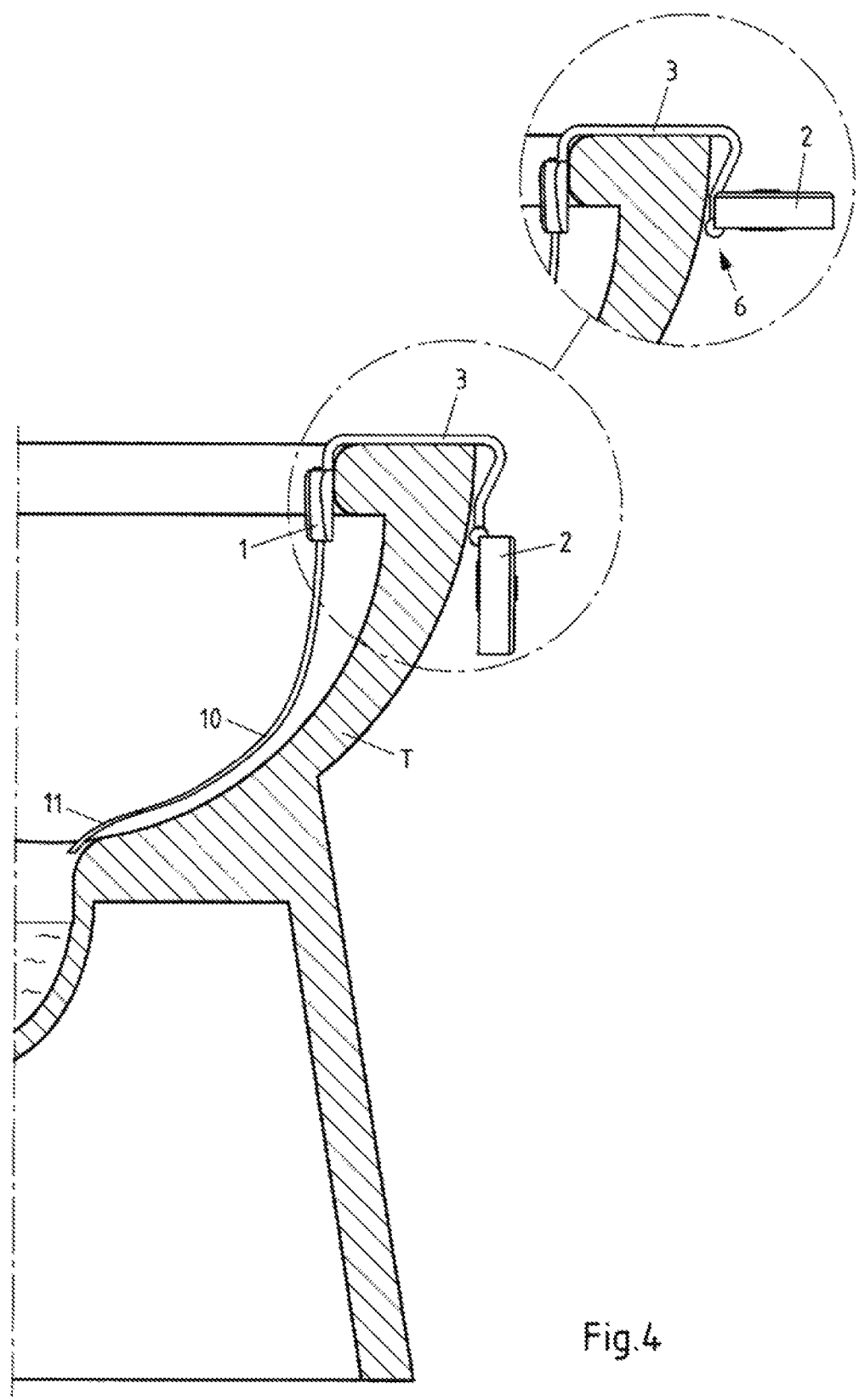
FIG. 4 shows a vertical cross-section through the device from FIG. 3 along the line IV-IV and FIG. 5 shows another embodiment of the device according to the invention, in the perspective of inside the toilet bowl.

In FIG. 4 the device according to the invention with housing 1, retainer 3 and control unit 2 is again represented with the toilet T represented in cross-section in its entirety in a vertical cross-section along the line IV-IV from FIG. 3, initially with the control unit 2 tilted downwards and, at the top right, with the control unit 2 tilted upwards about the hinge 6.

Figure 5:
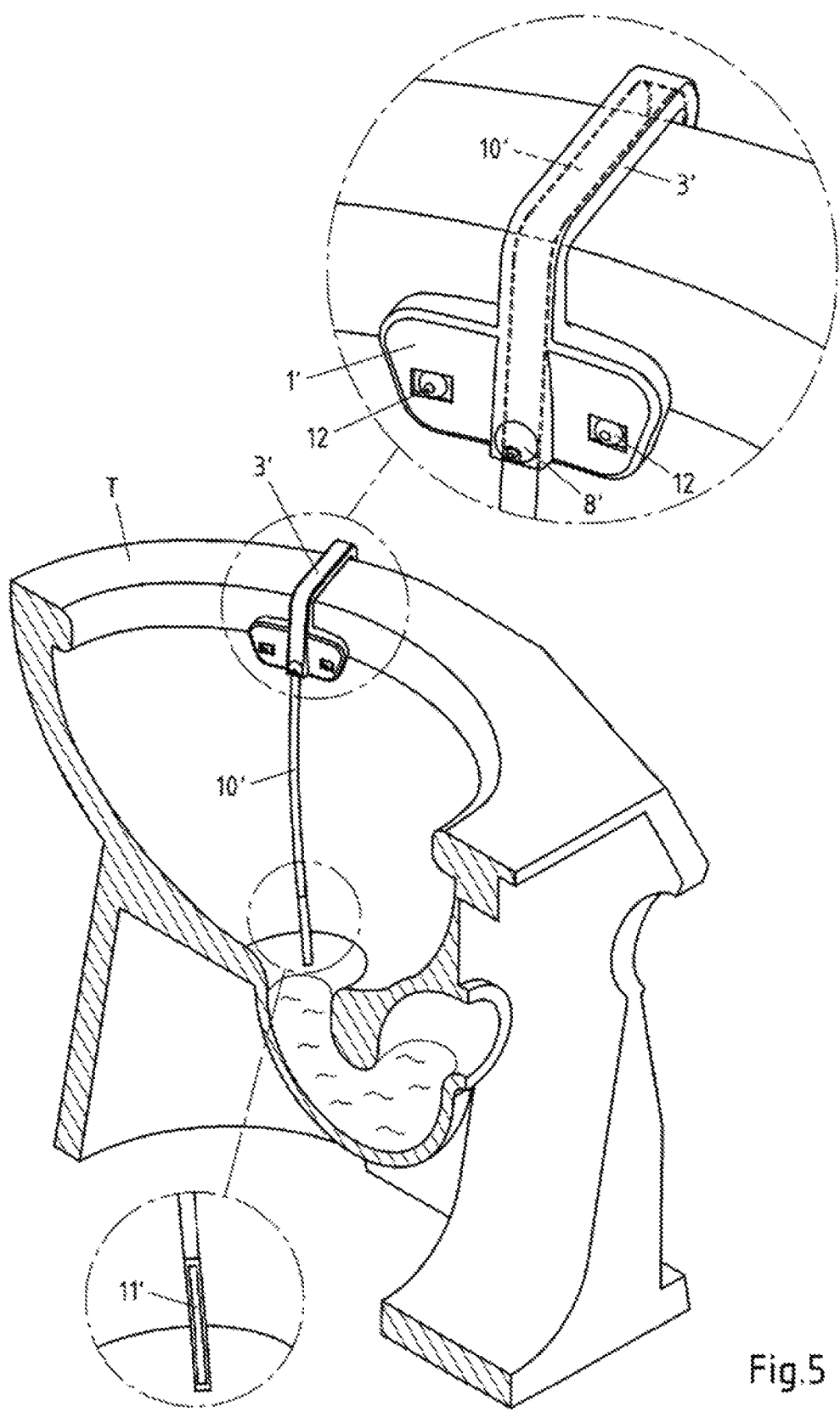
Figure 6:
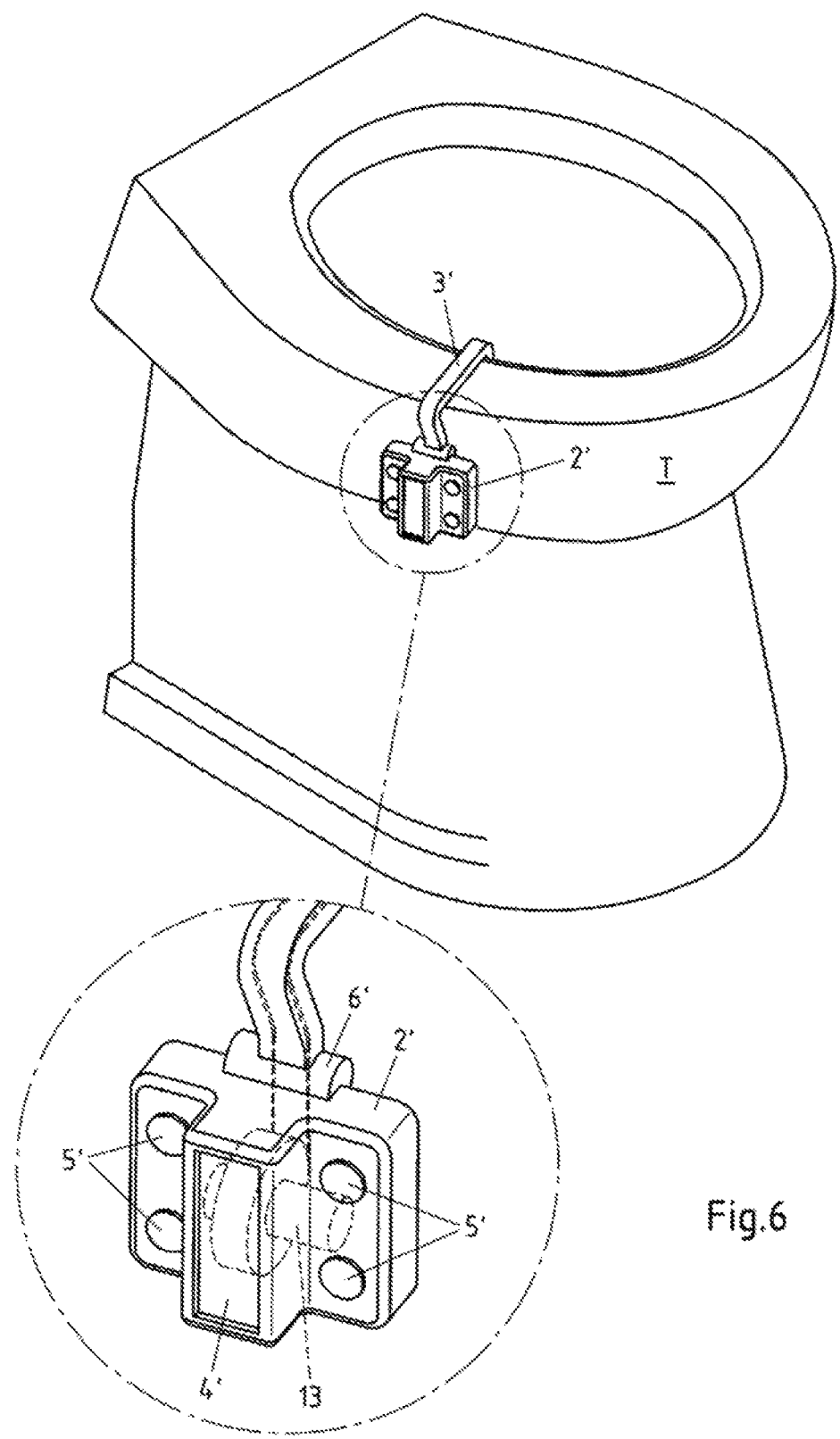
FIG. 6 shows the device from FIG. 5, in perspective from the outside

In FIGS. 5 and 6 another preferred exemplary embodiment of the device according to the invention is represented in a different perspective view. The measurement is carried out by means of a sensor arm 10', which comprises an indicator 11' on its end. The device comprises a housing 1', which in the represented and thus far preferred exemplary embodiment is provided with a measuring unit 8' and sensors such as cameras 12, for example. The housing 1' is arranged inside a toilet bowl T and connected to an evaluation and control unit 2' on the outer edge of the toilet bowl T by means of a retainer 3, expediently via a hinge arrangement 6'. The retainer 3' can thus be adjusted in its length in order to be able to fit different designs of toilet bowls. In the represented embodiment, the sensor arm 10' is guided by the evaluation and control unit 2' through the retainer 3 into the housing 1 inside the toilet.

This occurs with the aid of a drive 13 represented in the enlargement in FIG. 6, which in the represented and thus far preferred exemplary embodiment is arranged inside the evaluation and control unit 2'. The drive can also be arranged in the housing 1'. The sensor arm 10' is in a retracted position and unrolls when extending with the aid of the drive 13. When leaving the housing 1' inside the toilet, the sensor arm 10' as represented in FIG. 6 stiffens and can thus be moved to the measurement location in a targeted way. The stiffening is carried out through material properties and/or through mechanical deformation. For measuring, the measurement unit 8', which in this embodiment is arranged centrally above the outlet of the sensor arm 10', is used to optimally evaluate the indicator 11'. Two-line cameras 12 are arrange to the left and right of this, with the aid of which on the one hand the measurement time can be determined and on the other hand a volume flow measurement and/or a mass determination can be carried out.

The evaluation and control unit 2' further has a control display 4' and a plurality of operating elements 5' for carrying out the measurement and evaluation.

Figure 7:
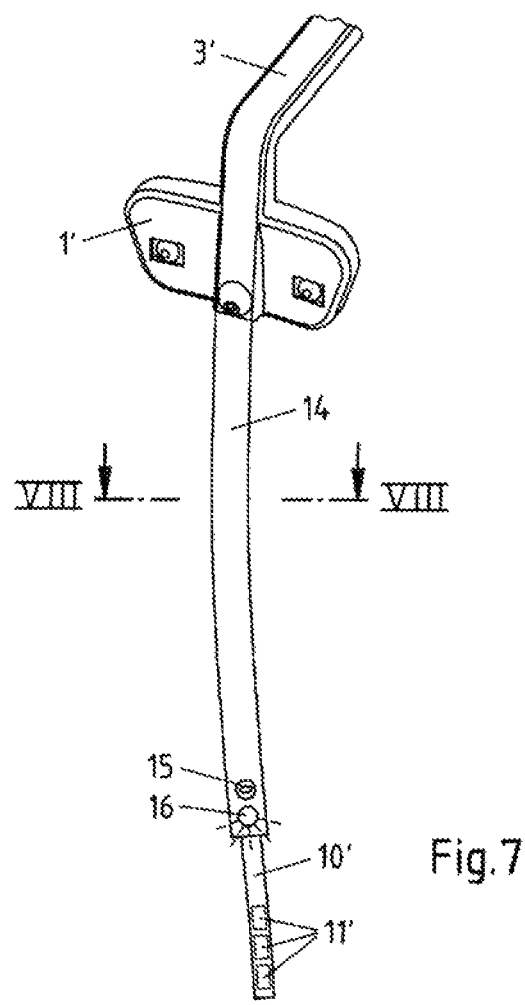
FIG. 7 shows a part of the device from FIG. 6, in perspective view.

An alternative embodiment is shown in FIG. 7. Thus, the sensor arm 10' is forcibly driven inside the toilet through an empty guide sleeve 14 into the inside of the toilet until the sensor arm 10' with the indicator(s) thereon has almost reached the measurement position. This embodiment can therefore do without a self-stiffening implementation of the sensor arm. In the represented and thus far preferred exemplary embodiment, a sensor 15 and a light source 16 are placed on the under end of the guide sleeve 14, the connection cables of which are also arranged on or preferably in the guide sleeve 14.

Figure 8:
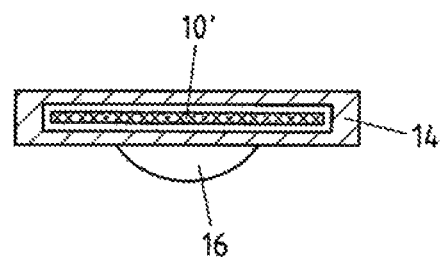
FIG. 8 shows a horizontal cross-section through the object from FIG. 7 along the line VIII-VIII.

FIG. 8 shows a cross-section of the guide sleeve 14 along the line VIII-VIII in FIG. 7. It can clearly be seen that the sensor arm 10' in this embodiment can be formed very thinly. In the exemplary embodiment represented in FIG. 7, it is shown that in the place of individual indicators, several different indicators 11' can be brought into use.

Figure 9:
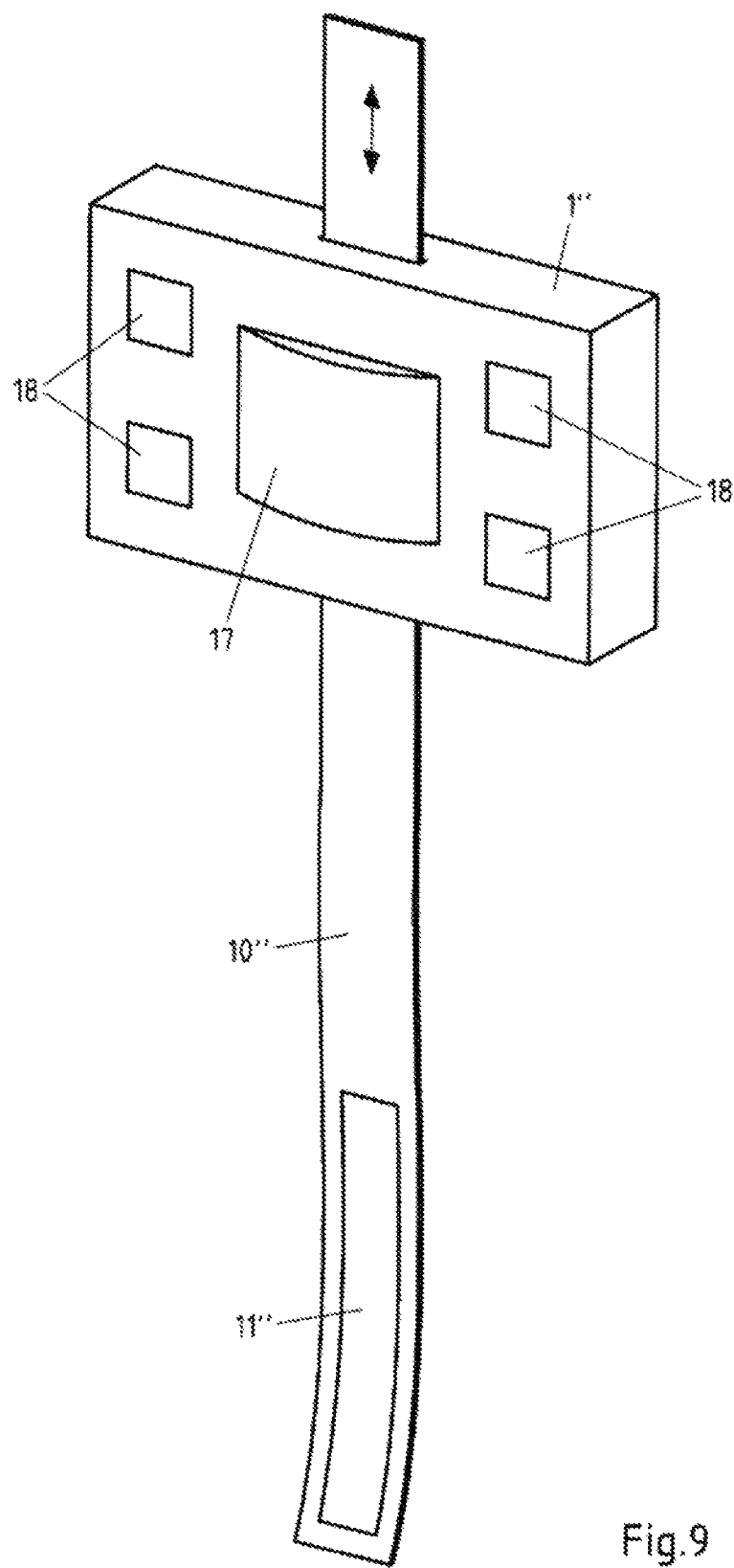
FIG. 9 shows a further embodiment of the device according to the invention.

Finally, FIG. 9 schematically shows a basic construction of a further embodiment of the device according to the invention in its most simple and rudimentary design. This initially and essentially consists of a sensor arm 10", which comprises an indicator 1' on its under end, and a housing 1" to hold, present and use the sensor arm 10". In the represented and preferred exemplary embodiment, the housing 1" has a viewing window 17 to compare and if necessary expand a measurement result with standard parameters, which—for example as colour marking 18—can be arranged directly on the housing 1" near the viewing window 17 for a simple, optical comparison.

The sensor arm 10" is moveable along the double arrow in relation to the housing 1" and for optical evaluation at the site of the contact with the excrement inside the toilet can be manually retracted so that the user can clearly and easily read from the actual indicator area. The housing 1" can thus be attached to the upper edge of a toilet bowl (not shown) with suitable attachment devices (not shows) such as suction pads or similar, for example.

The invention claimed is:

1. A device for determining physiological data through analysis of urine or stool in a toilet, comprising means of at least one indicator and/or sensor, in which for each measurement an indicator or sensor is moved into the inside of the toilet from the outer side of the toilet by means of a rollable arm that is reversibly configurable between a wound-up and an unwound form and is brought into a measurement position by means of an at least partially self-stiffening arm that stiffens when in said rollable arm is in the unwound form, in which sufficient contact with the urine or stool to be examined occurs.

2. Device according to claim 1, characterised in that one or a plurality of indicators or sensors are arranged in a housing and wherein the housing is reversibly attached to the toilet bowl.

3. Device according to claim 1, characterised in that the at least one indicator or sensor is formed as a single-use disposable indicator or single-use sensor.

4. Device according to claim 1, characterised in that the at least one indicator or sensor is formed as a multiple-use indicator or multiple-use sensor.

5. Device according to claim 1, characterised in that a plurality of indicators or sensors is provided and in that when gathering the indicators or sensors, at least one refillable magazine is provided.

6. Device according to claim 1, characterised in that the indicator or sensor arm are freed of waste excrement by means of a cleaning device.

7. Device according to claim 1, further comprising a UV light source.

8. Device according to claim 1, characterised in that the device comprises at least an optoelectrical unit and/or a sonographic unit.

9. Device according to claim 1, characterised in that the device comprises an evaluation device, a communication device and/or an analysis device.

10. A method for determining physiological data through analysis of human excrement in a toilet by measuring urine and/or stool values, with an indicator and/or sensor movable into the inside of the toilet from the outer side of the toilet by means of a rollable arm that is reversibly configurable between a wound-up and an unwound form and at least partially self-stiffening arm that stiffens when in said rollable arm is in the unwound form, in which sufficient contact with the urine or stool to be examined occurs, characterised in that a plurality of predetermined values are measured and automatically processed further and forwarded as applicable.

11. Method according to claim 10, whereby excrement quantity and volumes, as well as excrement volume or mass flows are determined through stereoscopic images.

12. Method according to claim 10, characterised in that the indicator or sensor is present in liquid form in the device and brought into contact with the sample or excrement by means of supply elements, such as a grid or a matrix, for example.

13. Method according to claim 10, further comprising the step of observing an indicator reaction, the indicator reaction being carried out over a determined duration and generating additional information.

14. Method according to claim 10, further comprising the step of determining an optimum measurement time through the device by means of individual sensors or a combination of heat sensors, optical evaluation and acoustic sensors.

15. Method according to claim 10, characterised in that automatic or guided calibration or adjustment is carried out to optimally install the device on the toilet and align it in the toilet.

16. Method according to claim 10, characterised in that the device is used for identifying a certain person (user) and after the measurement, the obtained measurement values are added to further vital and personal monitoring parameters.

17. Method according to claim 10, characterised in that the measurement and/or further processing of the measurement value is carried out automatically and the values are conveyed to an evaluation device.

18. Method according to claim 10 wherein said method for determining comprises one or more of the following examinations:
   determination of phase of a menstrual cycle,
   determination of blood alcohol level,
   evidence of pregnancy,
   evidence of drug consumption,
   (early) indication of benign or malignant tumours,
   monitoring of diets,
   checking of metabolism,
   checking of medications, and
   checking of standard urine values (urine quick test).

* * * * *